Figure 1:
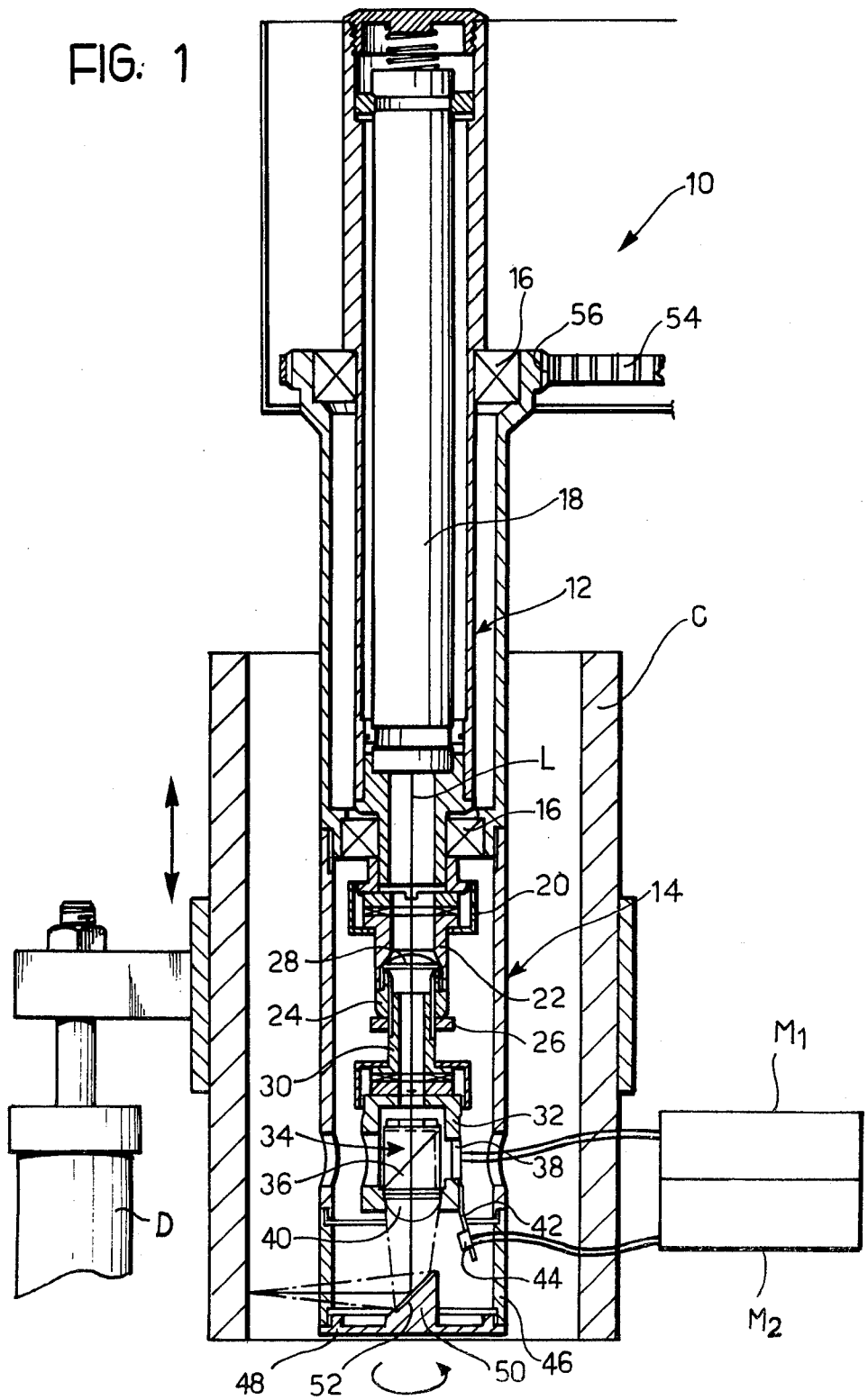

United States Patent [19]

Milana

[11] 4,440,496

[45] Apr. 3, 1984

[54] PROCESS AND DEVICE FOR INSPECTING AND CHECKING THE INTERNAL SURFACE OF A HOLLOW CYLINDRICAL WORKPIECE WHICH HAS UNDERGONE MECHANICAL WORKING

[75] Inventor: Emilio Milana, Rivalta, Italy

[73] Assignee: Fiat Auto S.p.A., Turin, Italy

[21] Appl. No.: 267,977

[22] Filed: May 28, 1981

[30] Foreign Application Priority Data

May 28, 1980 [IT] Italy .................... 67831 A/80

[51] Int. Cl.³ ............................................. G01N 21/88
[52] U.S. Cl. .................................... 356/241; 356/355
[58] Field of Search .................... 356/241, 355, 445

[56] References Cited

U.S. PATENT DOCUMENTS

| | | | |
|---|---|---|---|
| 3,749,496 | 7/1973 | Hietanen et al. | 356/241 |
| 3,761,186 | 9/1973 | Wason | 356/241 |
| 4,055,382 | 10/1977 | Ziekman et al. | 356/241 |
| 4,124,300 | 11/1978 | Mead et al. | 356/355 |

Primary Examiner—Vincent P. McGraw
Attorney, Agent, or Firm—Sughrue, Mion, Zinn, Macpeak & Seas

[57] ABSTRACT

A process for inspecting and checking the internal surface of a hollow cylindrical workpiece which has undergone mechanical working, particularly finishing by grinding or the like following which the internal surface has two sets of intersecting, helical score lines, consists in the examination of the diffraction pattern generated by laser radiation incident normally on the internal surface of the workpiece, so as to obtain a series of indications related to the characteristics of the two sets of intersecting helical score lines. The device for carrying out the process includes, as well as means for detecting the said diffraction pattern, means for providing an indication of the degree of roughness of and the presence of possible surface defects on the internal surface of the workpiece.

8 Claims, 3 Drawing Figures

PROCESS AND DEVICE FOR INSPECTING AND CHECKING THE INTERNAL SURFACE OF A HOLLOW CYLINDRICAL WORKPIECE WHICH HAS UNDERGONE MECHANICAL WORKING

The present invention relates in general to a process for inspecting and checking the surface of a workpiece which has undergone mechanical working. More particularly, the invention relates to a process for inspecting and checking the internal surface of a hollow cylindrical workpiece, particularly of a cylinder liner for internal combustion engines, which has undergone a finishing operation of grinding or the like as a result of which the internal surface of the workpiece has two sets of intersecting helical score lines or striations. As is known in this branch of the art, the characteristics and the correct disposition of the two sets of score lines on the internal surface of the cylinder liner for internal combustion engines is of fundamental importance as regards the circulation of the lubricant, the capacity of the piston rings to retain the lubricant and, in short, the wear of the cylinder liner.

The object of the present invention is thus to provide a process of the type specified above, which allows the simple, rapid and precise obtaining of a series of indications related to the characteristics of the two sets of intersecting helical score lines present on the internal surface of a hollow cylindrical workpiece which has undergone a mechanical finishing operation of grinding or the like, and which it is also possible to carry out directly in the production line to complete the quality control of the workpieces.

In order to achieve this object, the present invention provides a process for the inspection and checking of the internal surface of a hollow cylindrical workpiece which has undergone mechanical working, particularly a finishing operation of grinding or the like as a result of which the internal surface has two sets of intersecting, helical score lines, characterised in that it includes the steps of:

irradiating the internal surface of the workpiece with laser light in a direction normal to this surface, effecting relative rotational and translational movement of the workpiece and the radiation incident on the internal surface of the workpiece around and along the axis of the workpiece so as to explore the entire internal surface of the workpiece successively, detecting the diffraction pattern generated by the laser radiation incident on the internal surface of the workpiece by means of a photo-diode, the said diffraction pattern having a cruciform shape the arms of which intersect at angles corresponding to the angles of intersection of the two sets of score lines and rotate due to the effect of the relative rotational motion between the workpiece and the incident radiation, the said photo-diode being able to provide at its output an electrical signal as a function of time presenting a positive peak in correspondence with the passage of each arm of the said diffraction pattern over the photo-diode, forming from the said electrical signal an indication related to the characteristics of the two sets of intersecting helical score lines.

The process according to the invention makes it possible to obtain a series of indications relative respectively to the presence of both of the sets of score lines, the possible predominance of one set of score lines over the other, the value of the acute angle of intersection of the score lines of the two sets, and the value of the deviation of the bisector of the obtuse angle between the score lines and the two sets with respect to the generatrices of the workpiece. Furthermore, by means of the process according to the invention, it is possible to detect the undesirable presence of any remaining striations or score lines due to preceding rough working of the surface of the workpiece.

The invention also relates to a simple, practical and functional device which can be used directly in the production line for carrying out the process defined above.

According to the invention, a device for inspecting and checking, the internal surface of a hollow cylindrical workpiece which has undergone mechanical working, in particular a finishing operation of grinding or the like as a result of which the said internal surface has two sets of intersecting, helical score lines, is characterised in that it includes a cylindrical optical probe which can be inserted axially into the workpiece cavity and means for displacing the probe and the workpiece axially relative to each other, the said probe including:

an inner tubular part coaxially housing a laser radiation source and a telecentric optical system including a pair of axially-spaced lenses arranged to reduce the cross section of the beam of laser radiation leaving the said source, an outer tubular part coaxially and rotatably supported by the said inner tubular part and having a terminal part with a transparent wall carrying a mirror inclined to the axis of the probe and arranged to intercept the laser radiation coming from the said optical system and to deviate the said radiation radially onto the internal surface of the workpiece through the said transparent wall, means for effecting rotation of the outer tubular part relative to the said inner tubular part, a photo-diode carried by the inner tubular part in correspondence with the said transparent wall of the outer tubular part and arranged to detect the diffraction pattern generated by the laser radiation incident on the internal surface of the workpiece and to provide at its output an electrical signal indicative of the characteristics of the said two sets of intersecting score lines.

The electrical signal at the output of the photo-diode may to advantage be fed to an electronic micro-processor $M_1$ which is able to process this signal and provide indications relating to the presence of both sets of score lines, the possible predominance of one set of score lines over the other, the value of the acute angle of intersection between the score lines of the two sets, the value of the deviation of the bisector of the obtuse angle between the score lines of the two sets relative to the generatrices of the workpiece, and the possible presence of remaining undesirable score lines due to previous rough working of the surface of the workpiece.

The device according to the invention may further include, to advantage, a second photo-diode carried by the inner tubular part of the probe, an optical system for directing to the said second photo-diode the specular component of the radiation reflected by each point on the internal surface of the workpiece, the said second photo-diode being arranged to provide at its output an electrical signal indicative of the intensity of this component of the radiation, and electronic processing means $M_2$ fed by the output signals of the said second photosensor and arranged to provide an indication of the degree of roughness of the internal surface of the workpiece and the presence of possible surface defects. These two indications, by means of which it is possible to carry out complete quality control of the internal surface of the workpiece with a single piece of apparatus, may be obtained in a manner similar to that described and illustrated in U.S. Pat. Nos. 4,290,698, and 4,296,333.

Alternatively, these two indications may be obtained by means of a microprocessor processing system of conventional type.

Figure 2:
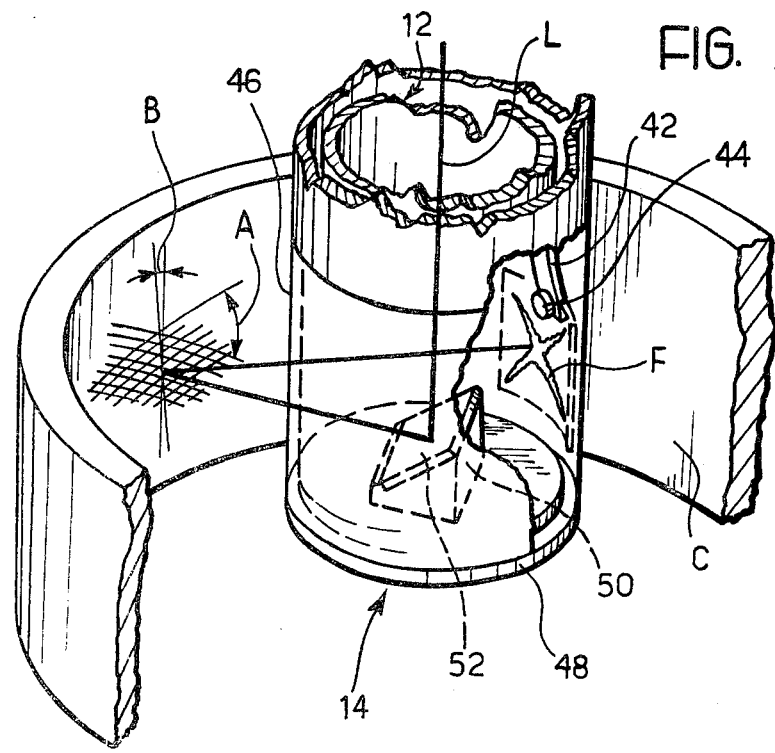
Figure 3:
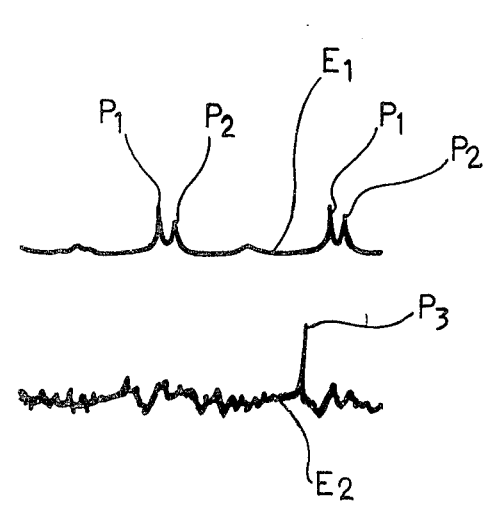

Further characteristics and advantages of the invention will become clear in the course of the following description, with reference to the appended drawings provided purely by way of non-limiting example, in which:

FIG. 1 is a schematic, partially-sectioned longitudinal view of a device according to the invention, FIG. 2 is a schematic perspective view illustrating, by way of example, the principle of operation of a part of the device illustrated in FIG. 1, and FIG. 3 is a diagram representing the electrical signals obtainable at the output of the device.

Referring to FIG. 1, by 10 is indicated in its entirety an optical probe for inspecting and checking the internal surface of a hollow cylindrical body C, for example the liner of a cylinder for an internal combustion engine, after the operations of finishing the internal surface of the body C.

The probe 10 is constituted essentially by an inner tubular support part 12 and an outer tubular casing 14 coaxial with and rotatable relative to the inner part 12 by means of rolling bearings 16. Within the upper zone of the inner part 12 is housed a laser radiation source 18 of conventional type, arranged to generate a laser radiation beam L directed along the axis of the probe 10 and towards the lower end of the probe 10.

Within the inner part 12 and below the laser source 18 there is inserted and locked by means of a series of sleeves and screw-threaded rings 20, 22, 24 and 26, a spherical lens 28, the focal axis of which is aligned with the axis of the probe 10. On the lower part of the sleeve 24 is screwed a further tubular element 30 which carries a tubular support block 32 at its lower end by means of a screw connection. Within the block 32 is inserted a beam-splitting cube 34 having a partially transmitting internal diagonal surface 36 inclined at an angle of 45° to the axis of the probe 10. This diagonal surface 36 is transparent to the laser radiation L coming from the source 18 and faces a photo-diode 38 disposed in an aperture in the side wall of the block 32. The photo-diode 38 is electrically connected, by means of conductors not shown, to an electronic processing circuit including a microprocessor of conventional type, not shown in the drawings, the operation of which will be described later on in the course of the description.

To the lower part of the support block 32, and hence below the beam splitting cube 34, is fixed a second spherical lens 40 the focal axis of which is aligned with that of the spherical lens 28. The two lenses 28 and 40 are so formed and disposed as to constitute a telecentric optical system adapted to reduce the diameter of the laser radiation beam L emitted by the source 18.

To the lower part of the support block 32 is fixed a support lug 42 carrying a further photo-diode 44 which is also electrically connected, by means of conductors not shown, to the said electronic processing circuit including the microprocessor. The photo-diode 44 is located in correspondence with an annular transparent wall zone 46 of the outer casing 14 of probe 10. This casing 14 has a lower base wall 48 transverse the axis of the probe 10 and having a central, upwardly-projecting axial support 50 carrying a mirror 52. The mirror 52 is inclined at 45° to the axis of the probe 10 and faces the transparent wall 46 of the casing 14.

The probe 10 is further provided with driving means for rotating the outer casing 14 with respect to the inner tubular part 12. These means may, for example, be constituted by an electric or pneumatic motor, not illustrated in the drawings, which effects rotation of a toothed belt 54 meshed with a toothed crown 56 formed on the outer surface of the upper end of the casing 14. These means for effecting the rotation of the casing 14 must be prearranged to give a high rate of rotation of the casing 14 and hence of the mirror 52, preferably a rate of between 2500 and 3000 rpm.

According to the invention there are also provided drive means for effecting relative axial displacement of the probe 10 and the cylindrical workpiece C in order to allow the entire internal surface of the workpiece to be explored successively during the rotation of the casing 14. For this purpose it is possible to provide a support for the workpiece C which is displaceable vertically with respect to the probe 10 by means of an hydraulic, pneumatic or any other type of conventional device D. Alternatively it is possible to provide a device for displacing the probe 10 axially, the workpiece C to be inspected being fixed.

The rotary movement of the casing 14 and of the probe 10 and the translationary movement of the workpiece C to be inspected may to advantage be controlled directly by the electronic microprocessor circuit which is connected to the photo-diodes 38 and 44.

The device according to the invention allows complete quality control of the internal surface of the cylindrical workpiece C, after carrying out the various mechanical working operations, to be achieved directly on the production line. A particularly advantageous application of the device is in the inspection and in the checking of cylinder liners for internal combustion engines subjected to finishing operations of grinding or the like as a result of which the internal surface of the barrel has two sets of intersecting, helical micro-scored lines or striations, the conformation and disposition of which is particularly important for the lubrication of the liner in use. The device according to the invention allows a series of indications related to the characteristics of the two sets of helical score lines of the barrel to be obtained and simultaneously allows indications relating to the degree of roughness of and the presence of possible surface defects on the internal surface of the workpiece to be obtained.

The first type of indication, that is, that related to the two sets of intersecting, helical score lines, is achieved by examination of the diffraction pattern generated by the laser radiation L incident on the internal surface of the workpiece by means of the electrical signal at the output of the photo-diode 44, which picks up this diffraction pattern through the transparent wall 46 of the casing 14 of the probe 10. FIG. 2 shows schematically the principle of this test. As is seen in this figure, the diffraction pattern or figure F generated by the laser radiation L, which intercepts the internal surface of the liner C normally, typically has the shape of an X the arms of which intersect at angles corresponding to the angles of intersection of the two sets of score lines. When the incident laser radiation moves with respect to the surface of the liner C, this diffraction pattern F rotates in an imaginary plane of observation, indicated in broken lines in FIG. 2. It is thus possible to obtain from a photo-diode disposed in this plane of observation, a signal, as a function of time, which has a positive peak in correspondence with the passage of each arm of the diffraction pattern F over the photo-diode itself. One example of the change in the electrical signal at the output of the photo-diode 44 as a function of time is shown schematically in the upper part of the diagram of FIG. 3. This signal, indicated by $E_1$, having positive peaks $P_1$, $P_2$ corresponding to the passage of the arms of the diffraction pattern F, is processed by the said electronic micro-processor circuit so as to obtain the following information relative to the two sets of intersecting helical score lines:

(a) the presence of both of the sets of score lines, through the verification of the presence of the peaks $P_1$ and $P_2$ in the signal, (b) any predominance of one set of score lines over the other, through a comparison of the heights of two successive peaks $P_1$, $P_2$ of the signal, (c) the value of the acute angle of intersection A between the score lines of the two rows, through the measurement of the time interval between one peak $P_1$ and the successive peak $P_2$ and through the angular rate of rotation of the rotating part 14 of the probe 10, (d) any angle of deviation B of the bisector of the obtuse angle between the score lines of the two sets with respect to the generatrices of the workpiece C, through the measurement of the time interval between a peak $P_1$, $P_2$ of the signal and a reference time, (e) the possible presence of remaining undesirable striations due to preceding rough working, through the presence of anomalous peaks in the signal.

The indications relating to the degree of roughness of the internal surface of the workpiece C and the presence of possible surface defects are obtained through the electrical signal at the output of the photo-diode 38. This photo-diode 38 is prearranged to detect the intensity of the component of the laser radiation specularly reflected by the surface of the workpiece C and which reaches the photo-diode 38 through the transparent wall 46 of the casing 14 as a result of reflection by the mirror 52, focusing by the spherical lens 40 and reflection by the semireflecting surface 36 of the beam splitting cube 34. One example of the change in the electrical signal at the output of the photo-diode 38 as a function of time is illustrated in the lower part of the diagram of FIG. 3. This signal, indicated by $E_2$, is fed to the microprocessor circuit which forms the average value from it and correlates this average value with a series of experimental theoretical curves, related to various values of average roughness, stored in the memory of the microprocessor. The principle of this type of analysis is substantially similar to that forming the subject matter of U.S. Pat. No. 4,290,698.

The indication relative to the presence of defects on the surface of the workpiece is obtained by processing the electrical signal $E_2$ at the output of the photo-diode 38 which has a peak $P_3$ every time the laser radiation intercepts a surface defect. The surface defect in fact constitutes a centre of absorption of luminous energy which generates a negative peak in the signal $E_2$ at the output of the photo-diode 38. This peak $P_3$ may be detected by the microprocessor through a variable electronic threshold. The principle of this process of detection is substantially similar to that forming the subject matter of U.S. Pat. No. 4,296,333.

Naturally it is possible to give the microprocessor circuit optional functions adapted to provide, through the signals $E_1$ and $E_2$ at the output of the photo-diodes 38 and 44, further useful indications, such as, for example, the localisation by means of reference coordinates of any surface defects, the total number of these defects, etc.

Naturally, the principle of the invention remaining the same, details of construction and of embodiments may be varied widely with respect to that described and illustrated, without thereby departing from the scope of the present invention.

I claim:

1. Process for inspecting and checking the internal surface of a hollow cylindrical workpiece which has undergone mechanical working, particularly a finishing operation of grinding or the like, as a result of which the said internal surface has two sets of intersecting, helical score lines, the process including the steps of:

directing a beam of laser radiation onto the internal surface of the workpiece normally to said surface to form a diffraction pattern;

effecting relative rotational and translational movement of the workpiece and the said incident laser beam respectively about and along the axis of the workpiece to scan the entire internal surface of the workpiece successively, detecting by photo-electric means the diffraction pattern formed by the laser radiation incident on said internal surface of the workpiece, said diffraction pattern having a cruciform shape the arms of which intersect at angles corresponding to the angles of intersection of the two sets of score lines and which rotate as a result of the relative rotation between the workpiece and the laser beam, the said photo-electric means providing an electrical output signal which as a function of time as a positive peak in correspondence with the passage of each arm of said diffraction pattern over the photo-electric means;

forming from the said electrical output signal an indication related to the characteristics of the two sets of intersecting helical score lines.

2. The process defined in claim 1, wherein the step of forming from the said electrical output signal an indication related to the characteristics of the said intersecting helical score lines consists in the measurement of the time interval between successive peaks of the electrical signal and obtaining, by means of the relative rotational movement between the workpiece and the incident radiation, the value of the acute angle of intersection between the score lines of the two sets.

3. The process defined in claim 1, wherein the steps of forming from said electrical signal an indication related to the characteristics of the said intersecting helical score lines consists in comparing the height of the two successive peaks of said electrical signal and obtaining an indication of the predominance of one set of score lines over the other.

4. The process defined in claim 1, wherein the step of forming from said electrical signal an indication related to the characteristics of the said intersecting helical score lines consists in measuring the time interval between a peak of said signal and a reference time and obtaining, by means of the relative rotational movement between the workpiece and the incident radiation, an indication of the deviation of the bisector of the obtuse angle between the score lines of the two sets with respect to the generatrices of the workpiece.

5. Device for inspecting and checking the internal surface of a hollow cylindrical workpiece which has undergone mechanical working, particularly a finishing operation of grinding or the like, as a result of which the said internal surface has two sets of intersecting helical score lines, said device including an optical probe insertable axially into the cavity in the workpiece and drive means for effecting relative axial displacement between the probe and the workpiece, the said probe including:

an inner tubular part,
a laser radiation source coaxially housed in said part and producing a laser beam,
and a telecentric optical system including a pair of lenses spaced apart along the axis of the probe and arranged to reduce the cross section of the laser beam emitted by said source,
an outer tubular part supported coaxially and rotatably by said inner tubular part and having a terminal part with a transparent wall,
a mirror disposed in correspondence with said transparent wall and inclined to the axis of the probe, said mirror being arranged to intercept the laser beam from said telecentric optical system and deflect said radiation radially onto the internal surface of the workpiece through said transparent wall,
drive means for effecting rotation of the said outer tubular part with respect to the said inner tubular part, and
photo-electric means carried by said inner tubular part in correspondence with said transparent wall of the outer tubular part and arranged to detect the diffraction pattern generated by the laser radiation incident on the internal surface of the workpiece and to provide an electrical output signal indicative of the characteristics of the said two rows of intersecting helical score lines.

6. The device defined in claim 5, and further comprising electronic processing means including a microprocessor adapted to receive the electrical output signal of the said photo-electric means and to provide an indication related to the presence of both of the sets of score lines, and to the predominance of one set of score lines over the other, the value of the acute angle of intersection between the score lines of the two sets, the value of the deviation of the bisector of the obtuse angle between the score lines of the two sets with respect to the generatrices of the workpiece, and the possible presence of striations resulting from preceding rough working.

7. The device defined in claim 5, wherein it further comprises:

a second photo-electric means carried by the inner tubular part of the probe,
an optical system for directing to the said second photo-electric means the specular component of the radiation reflected by each point of the internal surface of the workpiece, the said second photo-electric means being arranged to provide an electrical output signal indicative of the intensity of this radiation component, and
electronic processing means including a microprocessor adapted to receive the output signals of the second photo-electric means and to provide an indication of the degree of roughness of the internal surface of the workpiece and of the presence of surface defects thereon.

8. The device defined in claim 7, wherein said optical system includes said inclined mirror carried by the outer tubular part of the probe and a beam splitting cube interposed between the two lenses of said telecentric optical system and having a partially transmitting diagonal surface inclined to the axis of the probe and arranged to direct the said specular component of the laser radiation reflected by the internal surface of the workpiece to the said second phot-electric means, said component reaching the partially transmitting surface of the said beam splitting cube as a result of reflection by the said mirror and passage through one of said two lenses of the said telecentric optical system.

* * * * *